(12) United States Patent
Hallab

(10) Patent No.: US 10,588,681 B2
(45) Date of Patent: Mar. 17, 2020

(54) IMPLANT REMOVAL DEVICES AND METHODS OF USE THEREOF

(71) Applicant: RUSH UNIVERSITY MEDICAL CENTER, Chicago, IL (US)

(72) Inventor: Nadim James Hallab, Oak Park, IL (US)

(73) Assignee: Rush University Medical Center, Chicago, IL (US)

( * ) Notice: Subject to any disclaimer, the term of this patent is extended or adjusted under 35 U.S.C. 154(b) by 260 days.

(21) Appl. No.: 15/545,139

(22) PCT Filed: Jan. 20, 2016

(86) PCT No.: PCT/US2016/014096
§ 371 (c)(1),
(2) Date: Jul. 20, 2017

(87) PCT Pub. No.: WO2016/122938
PCT Pub. Date: Aug. 4, 2016

(65) Prior Publication Data
US 2018/0028248 A1    Feb. 1, 2018

Related U.S. Application Data

(60) Provisional application No. 62/107,584, filed on Jan. 26, 2015.

(51) Int. Cl.
*A61B 17/92*    (2006.01)
*A61F 2/46*    (2006.01)

(52) U.S. Cl.
CPC .......... *A61B 17/92* (2013.01); *A61F 2/4607* (2013.01); *A61F 2/4609* (2013.01); *A61F 2002/4619* (2013.01); *A61F 2002/4653* (2013.01)

(58) Field of Classification Search
CPC .......... A61B 17/92; A61F 2/46; A61F 2/4607
See application file for complete search history.

(56) References Cited

U.S. PATENT DOCUMENTS 4,373,263 A    2/1983 Ayers
5,290,291 A    3/1994 Linden
(Continued)

FOREIGN PATENT DOCUMENTS

WO    WO2006/020803 A2    2/2006

OTHER PUBLICATIONS

Jung et al. The Effects of Multiple Freeze-Thaw Cycles on the Biochemical Properties of the Human Bone-Patellar Tendon-Bone Allograft, Journal of Orthopedic Research, Mar. 4, 2011, p. 1194.
(Continued)

*Primary Examiner* — Christopher J Beccia
(74) *Attorney, Agent, or Firm* — Barnes & Thornburg LLP

(57) ABSTRACT

Various aspects of the present invention provide an apparatus and a method of removing an orthopedic implant from a patient. In one embodiment, the method includes cycling the temperature of at least a portion of the orthopedic implant between a first temperature and a second temperature that differs from the first temperature. In one embodiment, the first temperature is above 0° C. and the second temperature is below 0° C. The temperature cycling causes a thermal expansion differential between at least a portion of the orthopedic implant and material in a region contacting the orthopedic implant. In one embodiment, the thermal expansion differential is of an extent sufficient to cause physical separation of at least a portion of the surface of the orthopedic implant from material contacting the surface of the orthopedic implant.

15 Claims, 2 Drawing Sheets

(56) References Cited

U.S. PATENT DOCUMENTS

| | | | |
|---|---|---|---|
| 6,053,927 A | 4/2000 | Hamas | |
| 6,168,631 B1 | 1/2001 | Maxwell | |
| 6,258,090 B1 | 7/2001 | Jackson | |
| 6,872,643 B1 | 3/2005 | Halliyal et al. | |
| 8,182,506 B2* | 5/2012 | Fitz | A61B 17/0057 |
| | | | 606/200 |
| 8,419,640 B1 | 4/2013 | Saha | |
| 8,435,295 B2 | 5/2013 | Williams et al. | |
| 2013/0071813 A1* | 3/2013 | Braegger | A61C 8/0089 |
| | | | 433/173 |
| 2014/0128986 A1* | 5/2014 | Podolsky | A61F 2/3609 |
| | | | 623/22.4 |
| 2014/0285061 A1* | 9/2014 | McKinley | H01L 37/02 |
| | | | 310/306 |

OTHER PUBLICATIONS

PCT/US2016/014096, International Research Report and Written Opinion, 9 pgs.

* cited by examiner

IMPLANT REMOVAL DEVICES AND METHODS OF USE THEREOF

RELATED APPLICATIONS

This application is a National Stage of PCT/US2016/014096, filed Jan. 20, 2016, which claims the benefit of the filing date of U.S. Provisional Patent Application No. 62/107,584, filed Jan. 26, 2015, the contents of which applications are hereby incorporated by reference.

TECHNICAL FIELD

The present invention generally relates to an apparatus and a method for removing an orthopedic implant from a patient. In one embodiment, the apparatus is used to remove a metallic implant after tissue ongrowth.

BACKGROUND

Total joint replacement, particularly total hip and knee replacement, is being performed at an increasing rate. However, it is estimated that about 10% of these joints fail at the end of ten years, with an increased failure rate with longer years of implantation. In many total joint replacements, the implant is fixed to the patient's bone with the help of bone cement (for example, polymethylmethacrylate). In the revision surgery, the removal of the existing implant, reconstruction of the bone-stock and achievement of a stable fixation with a new component is often a difficult procedure. Bone cement is sometimes firmly bonded to the implant and surrounding bone, making it a technically demanding process to remove the implant without damaging the bone. For un-cemented hip and other joints, the implant is again firmly fixed to the bone, often due to on-growth of bony tissue onto the surface of the metal implant. The goal of such revision surgery is to remove the implant with minimum damage to the bone tissue so that the replacement implant is provided with sufficient support. Sometimes the difficulty in removing an implant causes the bone to fracture, and occasionally implant removal requires the surgeon to cut the bone itself to remove the implant.

Thus, the removal of orthopedic implants during revision surgery typically involves tissue destruction, long operative times and the use of great force with tools such as a slide hammer. Even poorly fixed orthopedic implants may be very difficult to remove because of adherent soft tissue that may be difficult to reach using bone sparing operative procedures. This process of implant removal is time consuming and difficult for the surgeon. This has made reversibility a central design feature of orthopedic implants where enhanced bone fixation technologies are not employed due to resulting difficulties in removal if required (as in, for example, fully porous coated stems). The force required to remove orthopedic implants can result in destruction of local bone stock making revision of an implant much harder, longer and subject to greater health risks to the patient, including an increased incidence of, for example, blood clots and stroke.

BRIEF SUMMARY

One aspect of the present invention provides a method of removing an implanted orthopedic implant from a patient. One embodiment of the method includes lowering the temperature of at least a portion of the orthopedic implant and of a region contacting a surface of the orthopedic implant from above 0° C. to below 0° C. In one embodiment, the lowering of the temperature is sufficient to freeze a region of tissue contacting the surface. In another embodiment, the region contacting a surface of the orthopedic implant is frozen to a depth of between 1 micrometer and 10,000 micrometers.

In such an embodiment, the temperature of the portion of the implant is then raised to above 0° C. within a time sufficiently short to cause a thermal expansion differential between the portion of the implant and material in the region contacting the surface of the orthopedic implant. The degree of the thermal expansion differential is sufficient to cause physical separation of at least a portion of the surface of the orthopedic implant from the material in the region contacting the surface of the orthopedic implant.

The implant may be subjected to a number of temperature cycles, where each temperature cycle varies the temperature of at least a portion of the implant in a cyclic manner between above 0° C. and below 0° C. within a time sufficiently short to cause a thermal expansion differential between the portion of the orthopedic implant and the region contacting the surface of the orthopedic implant and where the thermal expansion differential is sufficient to cause physical separation of at least a portion of the surface of the orthopedic implant from the region contacting the surface of the orthopedic implant. In one embodiment, the lowering the temperature of the implant and the region contacting a surface of the implant includes contacting the implant with a probe having a temperature below 0° C. for a time sufficient to lower the temperature of a surface of the implant and a region surrounding the surface of the implant to below 0° C.

In various embodiments, the temperature of the implant is cycled at a frequency of less than 100 Hz, or between 10 Hz and 100 Hz or between 50 Hz and 100 Hz. In another embodiment, the temperature of a least a portion of the implant is varied in a cyclic manner from above 2° C. to below −2° C. In yet other embodiments, the temperature of a least a portion of the orthopedic implant is varied in a cyclic manner over a range of at least 100° C. or 150° C.

The region surrounding the implant may include bone, tissue, bone cement or combinations of at least two of these materials. The implant may be, for example, a knee implant, a hip implant, a shoulder implant, a wrist implant, a spine implant, an elbow implant, a finger implant, an ankle implant, a fixation device, a plate, a rod or a screw. The implant may include a metallic material, for example, titanium, stainless steel, cobalt, chromium, zirconium or mixtures or alloys of at least two of these materials.

In another embodiment, the method includes cycling the temperature of at least a portion of the orthopedic implant and of a region contacting a surface of the orthopedic implant between a first temperature and a second temperature. In this embodiment, the temperature differential during the cycling is sufficient to cause a thermal expansion differential between the portion of the orthopedic implant and the region contacting the surface of the orthopedic implant. The thermal expansion differential causes a physical separation of at least a portion of the surface of the orthopedic implant from the region contacting the surface of the orthopedic implant.

Another aspect of the present invention provides an apparatus for facilitating separation of an orthopedic implant from tissue. One embodiment of the apparatus includes a heating/cooling unit and a transducer probe in thermal connection with the heating/cooling unit. In another embodiment, the heating/cooling unit and transducer probe in combination have a heat transfer capacity sufficient to cycle a metallic implant having a thermal capacity of ≤8000 J/K over a temperature range of ≤100° C. at a frequency of ≤100 Hz. The heating/cooling unit may be a thermoelectric heating/cooling unit.

BRIEF DESCRIPTION OF THE DRAWINGS

FIG. 1 also illustrates a cross-section of an exemplary orthopedic implant and surrounding bone region.

DETAILED DESCRIPTION

Definitions

Figure 1:
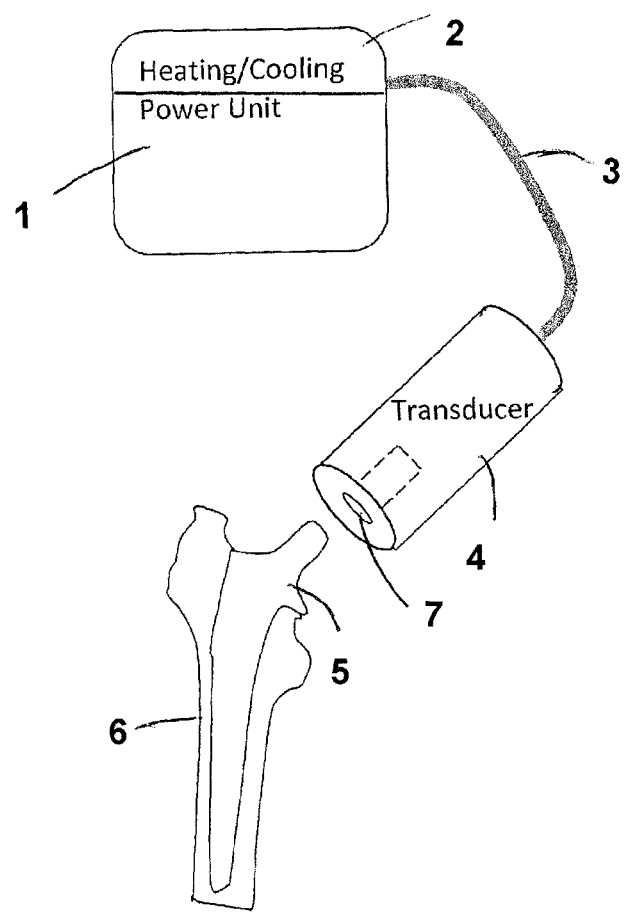
FIG. 1 is a schematic illustration of one embodiment of an apparatus of the present invention.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "patient" as used herein, refers to a human or veterinary patient, preferably a human patient.

Method for Removing an Orthopedic Implant from a Patient

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of an apparatus, methods of treatment, or other aspects, are disclosed. It is to be understood that each such disclosed feature or features can be combined with the generalized features discussed, to form a disclosed embodiment of the present invention.

One aspect of the present invention provides a method for removing a orthopedic implant from a patient. In one embodiment, the method includes separating the implant from surrounding material that adheres to the implant. Such material may include, for example, one or more of tissue, bone or bone cement. In another embodiment, the method includes at least weakening the adhesion between the implant and surrounding material, such as tissue, bone or bone cement. By providing for the separation or reduction in adhesion of such material, the method may reduce damage to the surrounding bone and tissue during removal of the implant. Preferably, the implant is a metallic implant. However, the method is generally applicable to any implant that is formed, or partly formed, from a material having heat transfer or thermal expansion characteristics that differ from those of the material surrounding the implant when implanted.

The method is applicable for the removal of various implants including, but not limited to, a knee implant, a hip implant, a shoulder implant, a wrist implant, an elbow implant, a finger implant, a spine implant or an ankle implant. The method is also applicable to the separation of load bearing bone/tissue contacting fixation devices including plates, rods and screws. The implant may include a metallic material such as, but not limited to, titanium, stainless steel, cobalt, chromium, zirconium and mixtures or alloys of at least two of these materials. The disclosed method is particularly applicable to the separation of an implant from the surrounding tissue, bone cement and/or bone.

One aspect of the present method includes the step of cycling the temperature of at least a portion of the orthopedic implant between temperatures sufficiently different to cause a thermal expansion differential between the implant and a region of material contacting the surface of the implant. The resulting expansion difference is of a magnitude sufficient to cause separation of a portion of the implant from the contacting material or at least a weakening of the bonding of the implant from the contacting material. The separation of the implant from the surrounding material may occur as the temperature of the implant is lowered and/or upon raising the temperature of the contacting surfaces (e.g. bone cement on metal implant contact). Separation of adhering material from the implant may allow for removal of the implant without, or with reduced, damage to the surrounding bone and/or tissue.

In one embodiment, the temperature of the implant and the region surrounding the implant is cycled between above 0° C. and below 0° C. Cycling the temperature in this manner results in the freezing of a region, for example a region of tissue material, surrounding at least a portion of the surface of the implant. The temperature of that portion of the implant is then raised to above 0° C. This temperature increase may be accomplished within a time that is sufficiently short to cause the thermal expansion differential between the orthopedic implant and the material in the region contacting the surface of the orthopedic implant. As is discussed further below, the cycling of temperature of the implant occurs over a temperature range and at a frequency sufficiently high to prevent heating or cooling of the surrounding bone/tissue to an extent that would cause tissue damage due to, for example, freezing or excessive heating of these materials.

In one embodiment, the high thermal conductivity of a metallic implant results in the difference in thermal expansion between the metallic implant and the cement/bone/frozen tissue surrounding the implant. This thermal expansion differential is sufficient to cause physical separation of at least a portion of the surface of the orthopedic implant from the material in the region contacting the surface of the orthopedic implant or at least a weakening of the bonding between the implant and the surrounding material. Such a physical separation acts to separate material in this region from the surface of the implant, resulting in at least a partial separation of the surface of the implant from surrounding tissue, bone cement and/or bone and, in doing so, facilitates the removal of the implant from the patient.

The implant may be subjected to the number of such temperature cycles. For example, the implant may be subjected to a number of temperature cycles each of which varies the temperature of at least a portion of the orthopedic implant in a cyclic manner between above 0° C. and below 0° C. The cyclic variation in temperature occurs within a time sufficiently short to cause a cyclic thermal expansion differential between the portion of the orthopedic implant and the material contacting the surface of the orthopedic implant and to cause physical separation of at least a portion of the surface of the orthopedic implant from the material contacting the surface of the orthopedic implant.

Such a cyclic variation in temperature may be achieved, for example, by contacting a surface of the orthopedic implant with a probe having a cyclic temperature variation and a thermal transfer capacity sufficient to cycle the implant through the required temperature variation. The temperature variation and cooling/heating transfer characteristics of the probe are such that the implant and surround region are subjected to the temporal temperature variation disclosed above.

In one embodiment, the probe is contacted with a surface of the implant for a time sufficient to lower the temperature of at least a portion of the implant and the surrounding region to a first temperature, for example to below 0° C. In various embodiments, the temperature of a region around at least a portion of the implant is reduced, for example to below 0° C., to a depth of, for example, 1 and 10,000 micrometers, or between 10 and 10,000 micrometers, or between 100 and 10,000 micrometers, or between 1,000 and 10,000 micrometers.

While maintaining the probe in contact with the implant, the temperature of the probe may be raised to a level sufficient to raise the temperature of that portion of the implant to a second temperature, for example to above 0° C., within a time sufficiently short to create a temperature differential between the implant and the surrounding region of tissue/cement/bone and to cause a separation of a surface of the implant from the surrounding tissue/cement/bone or at least a weakening of the binding between the implant and the surrounding material.

In various embodiments, the cyclic variation in the temperature of the probe is such that the temperature within the implant is varied between the maximum and minimum temperatures of the temperature cycle, for example, between above 0° C. and below 0° C., with a frequency of less than 100 Hz. In other embodiments, the frequency of the cyclic temperature variation is between 100 and 0.1 Hz; 10 and 0.1 Hz; 100 and 1 Hz; 10 and 100 Hz; 100 and 75 Hz; 50 and 10 Hz; 50 and 25 Hz or 50 and 40 Hz.

The maximum and minimum temperatures of the implant during the temperature cycling may be varied between, for example, 1° C. and −1° C.; 2° C. and −2° C.; 3° C. and −3° C. or 4° C. and −4° C. In other embodiments, the maximum and minimum temperatures of the implant during the temperature cycling differ by between, for example, 0.5 and 1° C.; 0.5 and 2° C.; 0.5 and 3° C.; or 0.5 and 4° C. In yet other embodiments, the maximum and minimum temperatures of the implant during the temperature cycling differ by greater than, for example, 1° C.; 2° C.; 3° C.; 4° C., 5° C., 6° C.; 7° C.; 8° C.; 9° C. or 10° C.

In other embodiments, there a greater magnitude of cyclic variation in the temperature of the implant. In such embodiments, the temperature is cycled at a frequency high enough so that the temperature of only a very thin portion of the material surrounding the implant is varied. For example, the cycling frequency may be sufficiently high so that the temperature of the surrounding material does not deviate significantly from the patient's normal body temperature (for example 37° C.) beyond a depth of between 1 and 10,000 micrometers, or between 10 and 10,000 micrometers, or between 100 and 10,000 micrometers, or between 1,000 and 10,000 micrometers. Such a high cycling frequency may prevent or reduce damage to the surrounding bone/tissue due to freezing, burning or deviation from normal body temperature.

For example, the temperature of the implant may be cycled between temperatures up to 200° C. and as low as −80° C., or up to 150° C. and as low as −50° C., or up to 100° C. and as low as −25° C., or up to 50° C. and as low as −15° C., or up to 50° C. and as low as −10° C. In other embodiments, the maximum and minimum temperatures of the implant during the temperature cycling differ by greater than, for example, 300° C.; 200° C.; 150° C.; 100° C.; 80° C., 60° C., 40° C.; 30° C.; 20° C. or 10° C. In further embodiments, the maximum and minimum temperatures of the implant during the temperature cycling differ by up to, for example, 300° C.; 200° C.; 150° C.; 100° C.; 80° C., 60° C., 40° C.; 30° C.; 20° C. or 10° C.

Separation of the implant from tissue may be enhanced by cycling the temperature of the implant and surround tissue between above freezing and below freezing. In such embodiments, the frequency of temperature cycling may be such that only a thin portion of the surrounding tissue is below 0° C. for a short time. For example, the temperature may be cycled at a frequency of up to 100 Hz or higher.

Another aspect of the present invention provides an apparatus for facilitating separation of an implant from tissue. Turning to FIG. 1, one embodiment of the apparatus includes a power unit 1 providing power to a heating/cooling unit 2. Heating/cooling unit 2 is in thermal contact with transducer probe 4 via connecting element 3. FIG. 1 also illustrates a cross-sectional view of artificial joint implant 5 positioned within bone 6. Transducer probe 4 is shown as having a concave contacting surface 7. Such a configuration may be advantageous in maximizing the contacting surface area, and the thermal transfer characteristics, when the transducer probe is used to contact a convex surface of an implant. However, the probe may be of any shape allowing for the required thermal contact between the probe and the implant. In some embodiments, the transducer probe may be supplied with a series of different shaped contacting surfaces that are interchangeable for use with implants having different shapes.

Figure 2:
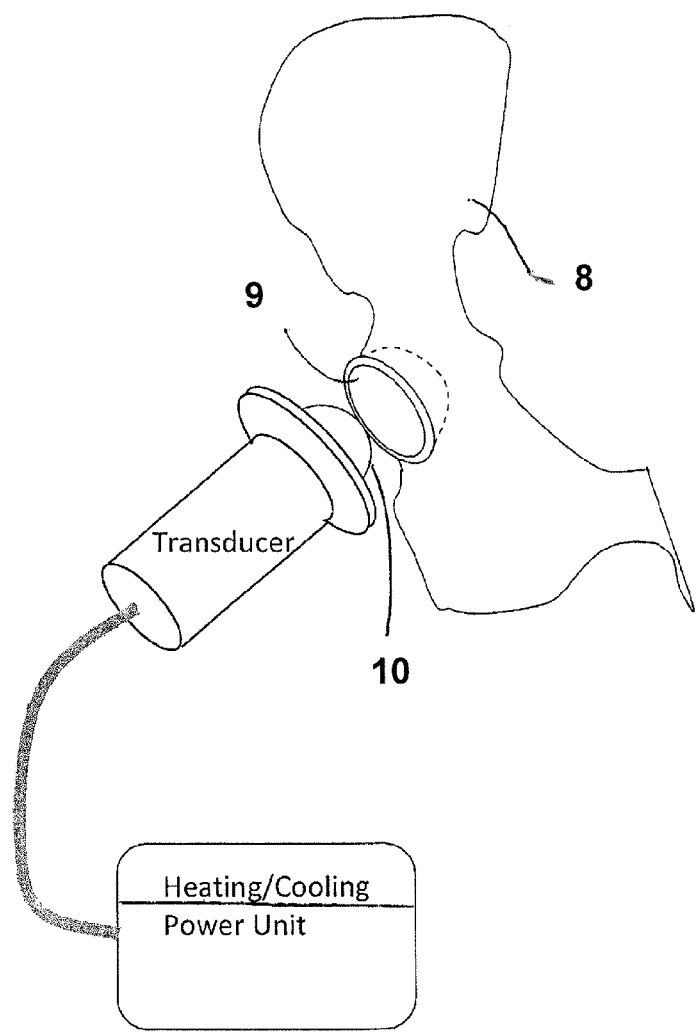
FIG. 2 is a schematic illustration of another embodiment of the apparatus of the present invention. This figure also includes an illustration of another exemplary implant and a portion of a surrounding bone region

FIG. 2 illustrates a similar apparatus with a transducer probe having a convex contacting surface 10. Such a contracting surface may be advantageous in maximizing the contacting surface area, and the thermal transfer characteristics, when the transducer probe is used to contact a concave surface of an implant, for example the concave surface of implant 9 in bone portion 8.

Heating/cooling unit 2 can be any device capable of supplying sufficient cooling/heating capacity to cycle the temperature of the implant and the surrounding region thorough the required temperature variation as disclosed above. For example, the heating/cooling unit cycler may be a thermoelectric heating/cooling unit, such as a Peltier cooler/heater. In other embodiments, the cooling capacity may be supplied by a conventional refrigeration unit, such as a vapor compression refrigeration unit. The required cooling capacity may also be supplied by utilizing a non-cyclic cooling source, such as liquid nitrogen. The heating capacity of the heating/cooling unit may also be supplied by, for example, filament heating or ultrasonic heating.

All that is required is that the heating/cooling unit has a capacity sufficient to raise and lower the temperature of the implant within the required timescale. In one embodiment, the heating/cooling unit, in combination with the probe, has a capacity sufficient to cycle the temperature of a metallic implant having a thermal capacity of ≤8000 J/K over a temperature range of ≤100° C. at a frequency of ≤100 Hz.

In other embodiments, heating/cooling unit has a capacity sufficient to cyclic the temperature of the implant over a temperature range of 300° C.; 200° C.; 150° C.; 100° C.; 80° C., 60° C., 40° C.; 30° C.; 20° C.; or 10° C. at a frequency of between 100 and 0.1 Hz; 10 and 0.1 Hz; 100 and 1 Hz; 10 and 100 Hz; 100 and 75 Hz; 50 and 10 Hz; 50 and 25 Hz or 50 and 40 Hz.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A method of removing an implanted orthopedic implant from a patient, the method comprising:
   lowering the temperature of at least a portion of the orthopedic implant and of a region contacting a surface of the orthopedic implant from above 0° C. to below 0° C., wherein the lowering is sufficient to freeze the region contacting the surface;
   raising the temperature of the portion of the orthopedic implant to above 0° C., wherein the raising of the temperature occurs in a time sufficiently short to cause a thermal expansion differential between the portion of the orthopedic implant and the region contacting the surface of the orthopedic implant and wherein the thermal expansion differential is sufficient to cause physical separation of at least a portion of the surface of the orthopedic implant from the region contacting the surface of the orthopedic implant; and
   subjecting the orthopedic implant to a plurality of temperature cycles, wherein the plurality of temperature cycles is at a frequency between 10 Hz and 100 Hz.

2. The method of claim 1, wherein:
   the temperature cycles vary the temperature of at least a portion of the orthopedic implant in a cyclic manner between above 0° C. and below 0° C.;
   the temperature cycles occur within a time sufficiently short to cause a thermal expansion differential between the portion of the orthopedic implant and the region contacting the surface of the orthopedic implant; and
   the thermal expansion differential is sufficient to cause physical separation of at least a portion of the surface of the orthopedic implant from the region contacting the surface of the orthopedic implant.

3. The method of claim 1, wherein lowering the temperature of at least a portion of the orthopedic implant and of a region contacting a surface of the orthopedic implant comprises contacting the orthopedic implant with a probe having a temperature below 0° C.; wherein the contacting is for a time sufficient to lower the temperature of a surface of the orthopedic implant and a region surrounding the surface of the orthopedic implant to below 0° C.

4. The method of claim 3, wherein the probe comprises a concave contacting surface.

5. The method of claim 1, wherein the plurality of temperature cycles is at a frequency between 50 Hz and 100 Hz.

6. The method of claim 2, wherein the temperature of a least a portion of the orthopedic implant is varied in a cyclic manner from above 2° C. to below −2° C.

7. The method of claim 2, wherein the temperature of a least a portion of the orthopedic implant is varied in a cyclic manner over a range of at least 100° C.

8. The method of claim 2, wherein the temperature of a least a portion of the orthopedic implant is varied in a cyclic manner over a range of at least 150° C.

9. The method of claim 1, wherein the region surrounding the orthopedic implant comprises a material selected from the group consisting of bone, tissue, bone cement and combinations of at least two of these materials.

10. The method of claim 1, wherein the orthopedic implant comprises a material selected from the group consisting of titanium, stainless steel, cobalt, chromium, zirconium and alloys of at least two of these materials.

11. The method of claim 1, wherein the orthopedic implant comprises titanium.

12. The method of claim 1, wherein the orthopedic implant is an implant selected from the group consisting of a knee implant, a hip implant, a shoulder implant, a wrist implant, an elbow implant, a finger implant, a spine implant, an ankle implant, a fixation device, a plate, a rod and a screw.

13. The method of claim 12, wherein the orthopedic implant is a hip implant.

14. The method of claim 1, wherein the region contacting a surface of the orthopedic implant is frozen to a depth of between 1 micrometer and 10,000 micrometers.

15. A method of removing an implanted orthopedic implant from a patient, the method comprising:
   cycling the temperature of at least a portion of the orthopedic implant and of a region contacting a surface of the orthopedic implant between a first temperature and a second temperature that differs from the first temperature for a plurality of temperature cycles;
   wherein the difference in temperature during the cycling is sufficient to cause a thermal expansion differential between the portion of the orthopedic implant and the region contacting the surface of the orthopedic implant and wherein the thermal expansion differential causes a physical separation of at least a portion of the surface of the orthopedic implant from the region contacting the surface of the orthopedic implant; and
   wherein the plurality of temperature cycles is at a frequency between 10 Hz and 100 Hz.

* * * * *